(12) United States Patent
Leigh

(10) Patent No.: US 9,228,893 B2
(45) Date of Patent: Jan. 5, 2016

(54) APPARATUS FOR MEASURING POLLUTANTS AND METHOD OF OPERATING THE SAME

(75) Inventor: Roland Leigh, Leicester (GB)

(73) Assignee: University of Leicester, Leicester (GB)

( * ) Notice: Subject to any disclaimer, the term of this patent is extended or adjusted under 35 U.S.C. 154(b) by 180 days.

(21) Appl. No.: 13/511,055

(22) PCT Filed: Dec. 1, 2010

(86) PCT No.: PCT/GB2010/052007
§ 371 (c)(1),
(2), (4) Date: Jul. 9, 2012

(87) PCT Pub. No.: WO2011/067599
PCT Pub. Date: Jun. 9, 2011

(65) Prior Publication Data
US 2012/0268739 A1    Oct. 25, 2012

(30) Foreign Application Priority Data
Dec. 1, 2009    (GB) .................................. 0921066.7

(51) Int. Cl.
*G01J 3/28*    (2006.01)
*G01J 3/02*    (2006.01)
(Continued)

(52) U.S. Cl.
CPC .. *G01J 3/02* (2013.01); *G01J 3/021* (2013.01); *G01J 3/0208* (2013.01); *G01J 3/0216* (2013.01);
(Continued)

(58) Field of Classification Search
CPC ............... G01J 3/02; G01J 3/10; G01J 3/18; G01J 3/28; G01J 3/2803; G01J 3/2823
USPC .................................................. 356/300–334
See application file for complete search history.

(56) References Cited

U.S. PATENT DOCUMENTS 5,159,199 A * 10/1992 LaBaw ..................... 250/339.02
5,608,526 A *  3/1997 Piwonka-Corle et al. .... 356/369
(Continued)

FOREIGN PATENT DOCUMENTS

CN        1995979 A     7/2007
CN     201133899 Y    10/2008
(Continued)

OTHER PUBLICATIONS

Stadlmeyer, R., "International Search Report" for PCT/GB2010/052007, as mailed May 20, 2011, 6 pages.
(Continued)

*Primary Examiner* — Abdullahi Nur
(74) *Attorney, Agent, or Firm* — Winstead PC

(57) ABSTRACT

A system for the detection of components in a region of the atmosphere is disclosed, the system comprising a spectrometer assembly having a detector optically coupled to a optical assembly, the optical assembly receiving incident sunlight from the region of the atmosphere, the optical assembly having a field of view extending from the zenith to below the horizon; means for rotating the spectrometer assembly about a vertical axis; and a processor for receiving data from the spectrometer assembly and compiling data relating to the identity and concentration of components in the region of the atmosphere. A method of monitoring pollutants in a region of the atmosphere comprises providing a spectrometer assembly having a detector optically coupled to an optical assembly having a field of view extending from the zenith to below the horizon; exposing the spectrometer assembly to incident sunlight while rotating the spectrometer assembly about a substantially vertical axis; and processing signals received from the spectrometer assembly to analyse components in the atmosphere. The system and method are particularly useful in monitoring atmospheric pollutants arising from the combustion of hydrocarbon fuels, in particular oxides of nitrogen and/or sulphur. A preferred arrangement comprises a plurality of systems disposed at spaced apart locations and having their scanned regions overlapping.

29 Claims, 10 Drawing Sheets

(51) Int. Cl.
*G01N 21/31* (2006.01)
*G01N 21/17* (2006.01)

(52) U.S. Cl.
CPC ............. *G01J 3/0289* (2013.01); *G01J 3/0291* (2013.01); *G01N 21/31* (2013.01); *G01N 2021/1795* (2013.01); *G01N 2201/0616* (2013.01)

(56) References Cited

U.S. PATENT DOCUMENTS

| | | | |
|---|---|---|---|
| 5,768,040 | A | 6/1998 | Macenka et al. |
| 5,807,750 | A | 9/1998 | Baum et al. |
| 6,542,242 | B1 | 4/2003 | Yost et al. |
| 2002/0175294 | A1 | 11/2002 | Lee et al. |
| 2003/0015019 | A1 | 1/2003 | O'Brien |
| 2008/0266687 | A1 | 10/2008 | Cook |
| 2009/0219528 | A1* | 9/2009 | Chamberlin et al. ......... 356/319 |

FOREIGN PATENT DOCUMENTS

| | | |
|---|---|---|
| DE | 202004005530 U1 | 7/2004 |
| WO | WO-2007/145554 A1 | 12/2007 |

OTHER PUBLICATIONS

Whyte, C., et al., "Assessment of the performance of a compact concentric spectrometer system for Atmospheric Differential Optical Absorption Spectroscopy", Atmospheric Measurement Techniques Discussions, vol. 2, Aug. 6, 2009, pp. 1901-1931.

Whyte, C. et al., "Assessment of the performance of a compact concentric spectrometer system for Atmospheric Differential Optical Absorption Spectroscopy", Atmospheric Measurement Techniques, 2, 2009, 789-800.

* cited by examiner

APPARATUS FOR MEASURING POLLUTANTS AND METHOD OF OPERATING THE SAME

The present invention relates to an apparatus for measuring the concentration of components in the atmosphere, in particular pollutants, and to a method of achieving the same. The present invention is especially concerned with determining the presence of and measuring the concentrations in the atmosphere of the products of the combustion of fuels, in particular, coal, oil and gas, together with the products of combustion of hydrocarbon fuels emitted in the exhaust gases of internal combustion engines.

There is a growing need for technology for monitoring, and hence managing, the toxic waste by-products produced during the fuel combustion process in the energy generation and transportation environments. In the United Kingdom, 77% of the energy consumed in the country is produced through the combustion of coal, oil or gas. In addition, the main modes of transportation in the country; cars, lorries, aeroplanes, trains and ships, all consume fossil fuels to produce energy. Waste products generated as a result of this energy production include $NO+NO_2$, (collectively referred to as $NO_x$), ozone, particulate matter, $SO_2$ and volatile organic compounds. These compounds are toxic and have been shown to have severe effects on human health.

Pollution may be defined as the contamination of the environment by man-made waste. $NO_2$ is one of the most prominent atmospheric pollutants and is a major cause of respiratory problems in urban areas. In particular, it acts as an irritant to the eyes, nose, throat and respiratory tract of people. The effects of ozone on human health are well documented and like $NO_2$, ozone affects the respiratory system causing an increase in asthma, reduced lung function and mortality. The adverse effects of pollutants such as $NO_2$ and ozone are particularly acute on the very young, the elderly and infirm, in particular those individuals with breathing or respiratory ailments.

The production of waste emissions from the combustion of petrol and diesel in cars, lorries, trains and aeroplanes is regulated at regional and national level. The United Kingdom is required to submit annual compliance reports to the European Commission under Article 11 (1)(a)(i) and Article (1)(a)(ii) of the Framwork Directive (1996/62/EC). As part of this national submission each county council is required to monitor and submit emissions, including $NO_2$ levels, to the Government.

In the United Kingdom, DEFRA recognises $NO_2$ as one of the best indicators of air pollution. The current state of the art in measuring $NO_2$ levels is to use either point sensors (1-D) or line measurements (2-D) where two sensors measure $NO_2$ in a line. Using this technology a significant number of sensors are required to characterise a given region. Certified calibrated sensors are sparsely located and expensive to maintain. As a result, any information generated is limited in its ability to identify the source of waste production or the movement and distribution of the waste products.

Accordingly, there is a need for an improved way of monitoring the atmosphere of a region or area, such as a town or city, that is able to provide an accurate indication of the concentration of pollutants in the atmosphere and its change over time. In particular, it would be advantageous if the apparatus employed could provide an accurate indication of pollutant concentration across the region and respond rapidly to changes in the concentration.

WO 2007/145554 is concerned with a method and apparatus for measuring the emissions gaseous substances in the atmosphere. The method and apparatus employ scattered sunlight spectroscopy. The method and apparatus use an optical measuring device having a field of view (FOV) and a scanning arrangement allowing a controlled variation in the direction of the FOV. In particular, the scanning arrangement allows a layer of the atmosphere to be scanned, the scanning layer being in the form of a cone having a specified cone angle and its apex at the optical measuring device. The apparatus may employ a spectrometer, for example a differential optical absorption spectroscopy (DOAS) system.

CN 1995979 A discloses a laser breakdown spectrographic detection method for identifying metal contaminants in water. The method uses short pulse laser accumulation to generate ions at the surface of the water. An optical spectrometer coupled to a CCD detector is employed to identify metal components in the water. There appears to be no suggestion that the system can be used for detecting components in a gaseous medium, such as the atmosphere.

U.S. Pat. No. 6,542,242 is concerned with a method and apparatus for mapping air contaminants. The method and apparatus employ path integrated optical remote sensing instruments to provide path integrated concentration (PIC) data relating to the particulate materials present in a scanned region. The method to acquire PIC data comprises the steps of using the instrument to generate a first path having a first length and then generating additional paths having different lengths within the sampling region. The method may be used to generate at least three paths of different lengths for a 1D reconstruction of the sampled region. In one embodiment, the method used to acquire PIC data generates a plurality of non-intersecting paths. In addition, the plurality of paths is preferably arrayed about a substantially common origin.

U.S. Pat. No. 5,807,750 discloses an optical substance analyser and processor. The analyser is of use in gas analysis for environmental control. The apparatus operates by collecting a sample and passing this to a single pass optical cell radiated by a light beam. The light beam is collected by a miniature CCD array spectrometer. The system may be used for extractive gas or liquid analysis.

A long optical path atmospheric monitoring instrument is described in CN 201133899. The apparatus comprises an optical generator having an emitter, a receiver and an optical assembly comprising a plurality of mirrors or prisms. Light from the optical assembly is processed by a spectrometer, a scanner and a processor.

US 2003/0015019 discloses a method and apparatus for analysing gas samples. The samples of gas are pneumatically focussed by the application of appropriate pressure and then analysed for content. Analysis may be by a variety of means, including spectrometry. The method is of use in the real-time monitoring of air quality.

An ultra-light miniature optical spectrometer is disclosed in DE 202004005530 U. The spectrometer is designed for use in an unmanned balloon deployed for atmospheric sampling and analysis. The spectrometer preferably has a large spectral detection range.

C. Whyte, R.J. Leigh et al., 'Assessment of the performance of a compact concentric spectrometer system for atmospheric differential optical absorption spectroscopy', Atmos. Meas. Tech. Discuss., 2 789-800, 2009, describe a demonstrator of a novel UV/VIS grating spectrometer for atmospheric research. The device is based upon a concentric arrangement of a spherical meniscus lens, concave spherical mirror and a curved diffraction grating. The device is suitable for remote sensing applications from the ground or from space.

There is a need for an improved system for monitoring atmospheric pollutants. In particular, there is a need for a system that can be operated from the ground, while still being able to monitor a large region of surrounding atmosphere. It would be particularly advantageous if the system could provide a real-time or substantially real-time image of atmospheric pollutants in the region being monitored. It would be particularly useful if the system could monitor the atmosphere for the presence of components produced by combustion processes, for example the combustion of hydrocarbon fuels.

According to a first aspect of the present invention, there is provided a system for the detection of components in a region of the atmosphere, the system comprising:

a spectrometer assembly having a detector optically coupled to a optical assembly, the optical assembly receiving incident sunlight from the region of the atmosphere, the optical assembly having a field of view extending from the zenith to below the horizon;

means for rotating the spectrometer assembly about a vertical axis; and a processor for receiving data from the spectrometer assembly and compiling data relating to the identity and concentration of components in the region of the atmosphere.

The system of the present invention is land-based and scans a region of the atmosphere extending around its location on the surface. The system employs incident sunlight, that is sunlight having passed through the region being scanned, to monitor the atmosphere. The system of the present invention detects components in the atmosphere throughout the region being scanned. By having the spectrometer assembly rotatable about a substantially vertical axis, the system is capable of scanning a region that extends in a horizontal arc about the system. Further, the spectrometer assembly has an optical assembly for receiving light having a field of view that extends in the vertical direction from the zenith to below the horizon. Thus, the system allows the components of the atmosphere in the region to be monitored in three dimensions around the location of the system. In addition, the system allows for changes in the concentration of components in the region to be monitored. In this way, the system of the present invention allows for a region of the atmosphere extending from and around the location of the system to be monitored for the presence of components in the atmosphere on a continuous basis, providing data relating to the identity and concentration of components in the atmosphere, as well as the changes in concentration over time.

The system of the present invention may be used alone. Alternatively and, in many cases, more preferably, two or more systems are employed at spaced apart locations, such that the regions scanned by the systems overlaps. This is particularly advantageous in the monitoring of pollutants, such as the products of the combustion of hydrocarbon fuels, in particular allowing for a tomographical analysis of the region.

In a further aspect, the present invention provides a method of monitoring pollutants in a region of the atmosphere, the method comprising:

providing a spectrometer assembly having a detector optically coupled to an optical assembly having a field of view extending from the zenith to below the horizon;

exposing the spectrometer assembly to incident sunlight while rotating the spectrometer assembly about a substantially vertical axis; and processing signals received from the spectrometer assembly to analyse components in the atmosphere.

The size of the region scanned by the system of the present invention will depend upon such factors as the sensitivity of the spectrometer to incident light and the arrangement of the optical assembly collecting the incident light. However, it has been found that the system of the present invention can accurately provide data for components in a region of the atmosphere extending for upwards of 75 $km^2$, that is a circle of radius 5 km, around the location of the system with a spatial resolution of 50 meters. When two systems are employed, the region of intersection of the two systems can be upwards of 25 $km^2$, allowing for an accurate tomographical monitoring of the region and the components in the atmosphere. The temporal resolution of the system will depend upon such factors as the nature and speed of the processor. However, it has been found that the system of the present invention can provide data on the composition of the atmosphere in the region being scanned at a temporal resolution of as low as 1 minute, that is indications of changes in composition of the atmosphere within the region can be provided at intervals as low as 1 minute to users and operators.

The components of the atmosphere to be detected by the system will depend upon the spectrometer. The system of the present invention may be arranged to detect one or more of a wide range of components in the atmosphere, depending upon the selection of the spectrometer. The system may be arranged to detect different components by being configured to resolve and detect light in different ranges of the electromagnetic spectrum, including light in the visible range as well as light in the non-visible range, such as ultra-violet. The system of the present invention is particularly suitable for the detection of pollutants in the atmosphere and the monitoring of pollution in the region being scanned. In particular, the system of the present invention is particularly advantageous in the monitoring of the products of combustion of fuels, in particular hydrocarbon fuels. It is especially preferred that the system of the present invention is configured to detect the presence and concentration of oxides of nitrogen and sulphur, both products of the combustion of hydrocarbon fuels. In addition or alternative to the products of fuel combustion, other components that may be detected using the system of the present invention include particulate matter and aerosols, ozone, glyoxal and iodine oxide using light in the visible spectrum. In this respect, aerosols include suspended materials, such as soot, sulphates and dust, as well as secondary organic aerosol compounds. Light in the ultra-violet spectrum may be used to detect components such as ozone, formaldehyde and a range of halogen oxides, including oxides of iodine, chlorine and bromine. Further, light in the infra-red spectrum may be used to detect components such as methane and carbon dioxide, both significant gases understood to contribute to the greenhouse effect and therefore two key components to be identified when monitoring levels of pollution in the atmosphere.

The system of the present invention comprises a spectrometer assembly. Suitable spectrometers are known in the art and are commercially available. One particularly preferred spectrometer assembly is a differential optical absorption spectroscopy (DOAS) system, preferably a concentric spectrometer configured for DOAS. Similar DOAS systems are known in the art and are commercially available. The system may comprise a single spectrometer covering a single wavelength range, for example the visible range of wavelengths. Alternatively, the system may comprise two or more spectrometers, thereby allowing the system to detect and monitor the presence of several components in the atmosphere across a wide wavelength range. A multiple-spectrometer arrangement may be required in order to provide a desirable level of data relating to a range of different pollutants in the atmosphere.

The spectrometer assembly comprises a detector to respond to the light entering the spectrometer assembly. Any suitable detector may be used and suitable detectors are commercially available. Preferably, the detector is a charge-coupled device (CCD) detector or a complementary metal-oxide-semiconductor (CMOS) detector. The detector may have any suitable readout strategy. Examples of suitable readout strategies include a split frame transfer (FT) device through either 2 or 4 nodes, a simple FT device through 2 nodes, a non-FT device employing a mechanical shutter, an liquid crystal display (LCD) shutter, or a beam deflector.

The detector receive light from the optical assembly and generates an electrical signal in response thereto. The detector is responsive to incident light of certain wavelengths, the range of wavelengths being determined by the components being identified in the atmosphere being monitored. The spectrometer assembly may be configured to respond to light of one or more wavelengths or ranges of wavelengths. For example, the assembly may be responsive to light in the visible spectrum, that is from about 380 to 750 nm, to light in the infra-red spectrum, that is from about 700 nm to 1 mm, more specifically from 1 to 2.5 µm for short wave infra-red retrieval, and the ultra-violet spectrum, that is from about 10 nm to 400 nm. Typical wavelength ranges are from 400 to 600 nm for the detection of oxides of nitrogen, in particular $NO_2$, ozone, particulate matter, glyoxal and iodine monoxide, and from 300 to 400 nm for increased ozone sensitivity and the detection of halogen oxides. Wavelengths in the general range of from 750 nm to 100 µm may be used for the detection of components such as carbon dioxide and methane, with specific wavelengths for carbon dioxide being 1.6 and 2.05 µm, and for methane 2.3 µm.

The detector is optically coupled to an optical assembly. The optical assembly collects and gathers incident light from the region being scanned, which is passed to the detector for analysis. Any suitable optical assembly may be employed. The optical system comprises an entrance slit through which incident light enters the system. Further, the optical assembly comprises one or more of each of a mirror, lens and grating, by means of which the incident light entering the slit is collected, dispersed by wavelength and focussed on the focal plane of the detector. The optical assembly preferably is of a concentric arrangement, that is the mirror, lens and grating are curved and arranged concentrically with respect to one another. This arrangement has been found to provide a particularly efficient optical system for collecting and collating the incident light for detection within the spectrometer.

As noted, the spectrometer assembly comprises entrance optics and an entrance slit for collecting incident sunlight. Any suitable entrance optics configuration may be used such that a focussed image from a wide field of view is formed along the length of the spectrometer entrance slit. One such system suitable for the system of the present invention utilises two aspheric mirrors in a Schwarzchild configuration.

The entrance optical assembly of the system has a field of view that extends from the zenith of the system to below the horizon, that is, the field of extends in an arc from the zenith of greater than 90°. Preferably, the field of view is at least 92° from the zenith, more preferably at least 95° from the zenith. In this way, the field of view extends up to 5° below the horizon. The width of the field is typically determined by the entrance optical assembly and is preferably from 0.1 to 1°, more preferably about 0.5°. In general, a lower width of the field of view is preferred to increase the angular resolution of the optical assembly. However, this can affect the speed and/or number of measurements that are required to be recorded by the system, in order to produce the desired information. Alternatively, the width of the field of view may be increased, in turn allowing the spectrometer assembly to rotated at a higher speed, as discussed in more detail below, and/or increasing the frequency measurements are taken. However, this increase in the width of the field of view also decreases the angular resolution of the optical assembly, in turn reducing the resolution and spatial accuracy of the system.

The spectrometer assembly is preferably arranged to provide data from a plurality of resolved elements across the entire field of view. In this way, data for the entire field of view of the spectrometer assembly may be produced. The combination of suitable entrance optics, providing parallel entrance illumination, coupled with an imaging spectrometer enables elements to be resolved at the focal plane of the detector. The greater the number of resolved elements across the field of view, the higher the overall resolution of the spectrometer assembly. Preferably, the field of view is divided into at least 100 resolved elements, more preferably at least 200, still more preferably at least 300 resolved elements. Most preferably, the field of view is divided into 500 resolved elements or more. For a field of view of 95°, this corresponds to 0.19° for each resolved element. The number of resolved segments will depend upon such factors as the optical quality of the components used in the system and the configuration and layout of the components of the optical system.

A combination of a concentric optical assembly, as described above, with an aspheric entrance optical assembly and a CCD detector has been found to be particularly suitable for the monitoring of pollutants in the atmosphere, for example in a system of the first aspect of the present invention.

Accordingly, in a further aspect, the present invention provides a spectrometer assembly for monitoring pollutants in the atmosphere, the spectrometer assembly comprising:
  an aspheric entrance optic assembly;
  a concentric optical assembly; and
  a CCD detector.

As noted above, the system of the present invention comprises means for rotating the spectrometer assembly about a substantially vertical axis. Any suitable means for rotating the spectrometer assembly may be employed. In one preferred embodiment, the spectrometer assembly is mounted on a turntable rotated by means of a motor, in particular an electric motor, for example connected to the turntable through a suitable gearbox or transmission, to allow the speed of rotation of the spectrometer to be finely controlled.

The spectrometer assembly may be arranged to rotate through 360°, that is a full circle, or less than 360°. Most preferably, the spectrometer is rotatable through a full rotation, allowing the system to provide data from a hemispherical region surrounding the location of the system. The system of present invention relies upon incident sunlight. In many cases, it will be necessary to avoid direct sunlight impinging on the optical system, as this will saturate the detector and may damage the spectrometer. Rather, it is preferred to use diffused sunlight and avoid pointing the spectrometer assembly directly at the sun. Accordingly, it is most preferred to provide a means for avoiding direct sunlight impinging on the optical assembly. Preferably, the system is arranged to allow the spectrometer assembly to be rotated for less than 360°, in order to avoid the optical assembly pointing directly at the sun and to avoid direct sunlight from entering the spectrometer assembly. Accordingly, it is preferred that the rotation of the spectrometer assembly is controllable to cover an entire rotation, with the exception of the arc allowing direct sunlight to enter the entrance optical assembly.

The spectrometer assembly is preferably provided with a protective covering, for example by being disposed within a housing, having at least a portion that is transparent to light of the wavelengths being detected by the assembly. In one embodiment, the spectrometer assembly is provided with a transparent dome thereover. Alternatively, the spectrometer assembly may be disposed within a housing having a transparent window aligned with the entrance optical system, the window being large enough to accommodate the entire field of view of the spectrometer assembly.

The system further comprises a processor for receiving electrical signals from the detector, for example the CCD detector and processing the signals to generate data relating to the identity and concentration of the components in the atmosphere being monitored. Suitable processors are known in the art and are commercially available. The processor is preferably provided with a memory or data storage means. This is particularly the case, as the system may be employed during daylight hours, that is up to 16 hours per day or longer, resulting in the processor producing a significant amount of data. The processor may be arranged to provide processing of the data, for example complete processing for output and display locally to the system and/or for transmission to a central device, such as a server, for further processing and/or display remote from the system. In a preferred embodiment, the data are presented graphically or by way of images, indicating the nature and concentration of components in the atmosphere being monitored.

In one embodiment, the system of the present invention is arranged to detect the concentration of one or more target components, in particular the products of combustion of hydrocarbon fuels, and the processor is configured to generate estimates of emission levels of the target components in the region being scanned.

The system of the present invention may be employed individually to scan a particular region of the atmosphere. Alternatively, two or more systems may be employed to scan overlapping regions of the atmosphere. In this way, data representing the tomography of the region of overlap may be obtained, providing an improved indication of the components present in the atmosphere.

Embodiments of the present invention will now be described, by way of example only, having reference to the accompanying drawings, in which:

FIG. 2b is a plan view of the spectrometer assembly of FIG. 2a;

Figure 1:
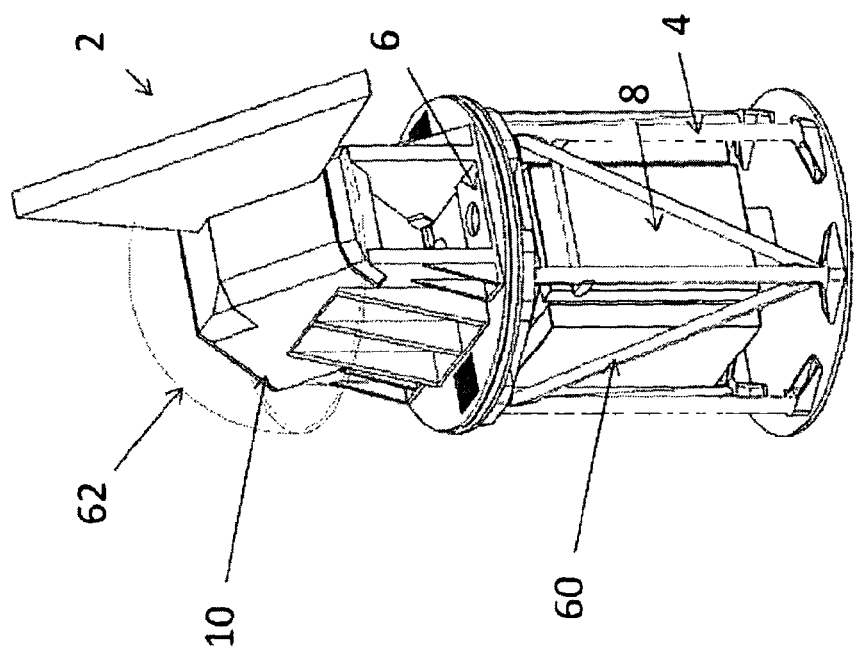
FIG. 1 is a perspective view of a system according to one embodiment of the present invention.

Turning to FIG. 1, there is shown a system according to one embodiment of the present invention, generally indicated as 2. The system 2 comprises a base assembly 4, having a turntable 6 mounted thereon and driven by a motor assembly 8 located in the base assembly 4. A spectrometer assembly 10 is mounted on the turntable 6, so as to be rotatable therewith by the motor assembly 8.

Figure 2A:
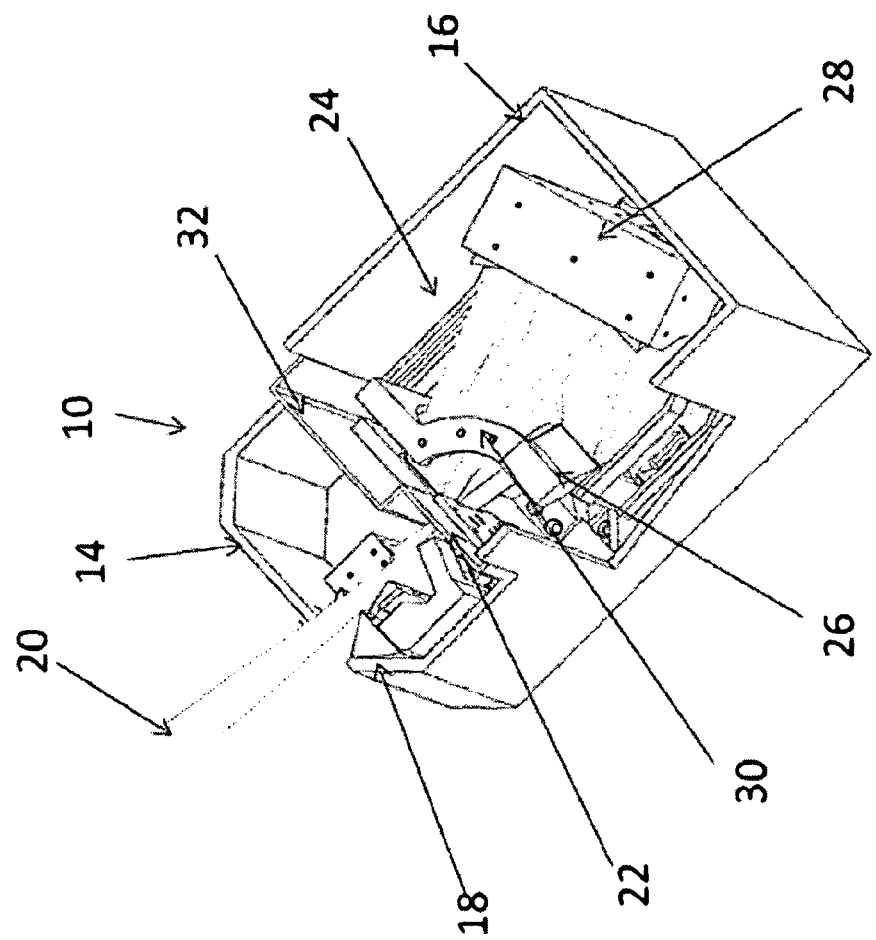
FIG. 2a is a perspective view of the spectrometer assembly of the system of FIG. 1.
Figure 2B:
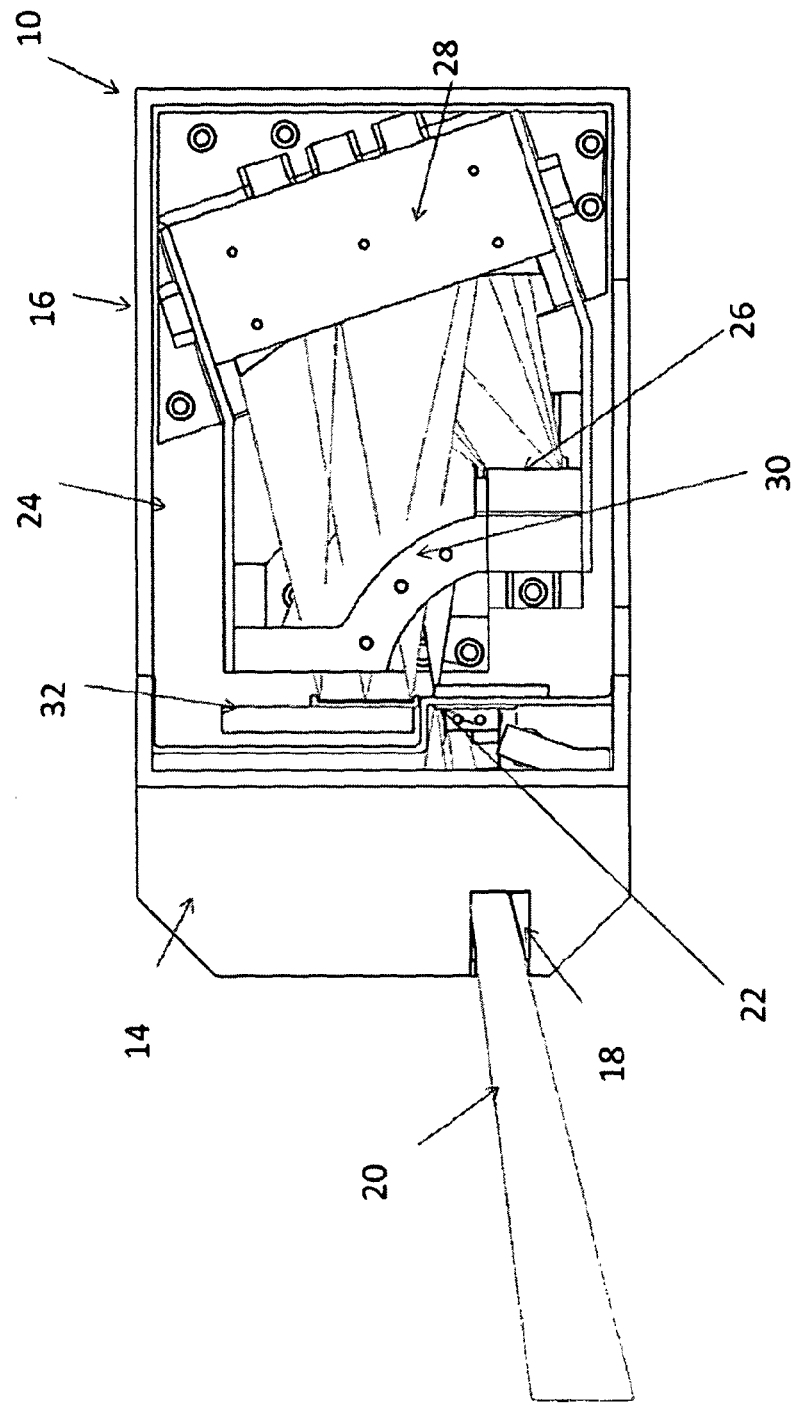

The spectrometer assembly 10 is shown in more detail in FIGS. 2a and 2b. The spectrometer assembly 10 comprises a generally rectangular housing 12 having a first housing portion 14 and a second housing portion 16. The first housing portion is provided with an opening 18 therein for the ingress of incident light. Incident light entering the spectrometer assembly 10 is shown as feature 20 in the accompanying figures. An entrance optical assembly 22 having an entrance slit is disposed in the first housing portion 14 and receives light entering the opening 18.

An optical assembly, generally indicated as 24 and comprising a grating assembly 26, a mirror assembly 28 and a lens assembly 30, is disposed within the second housing portion 16, together with a detector 32, details of which are described hereinbelow.

Figure 3:
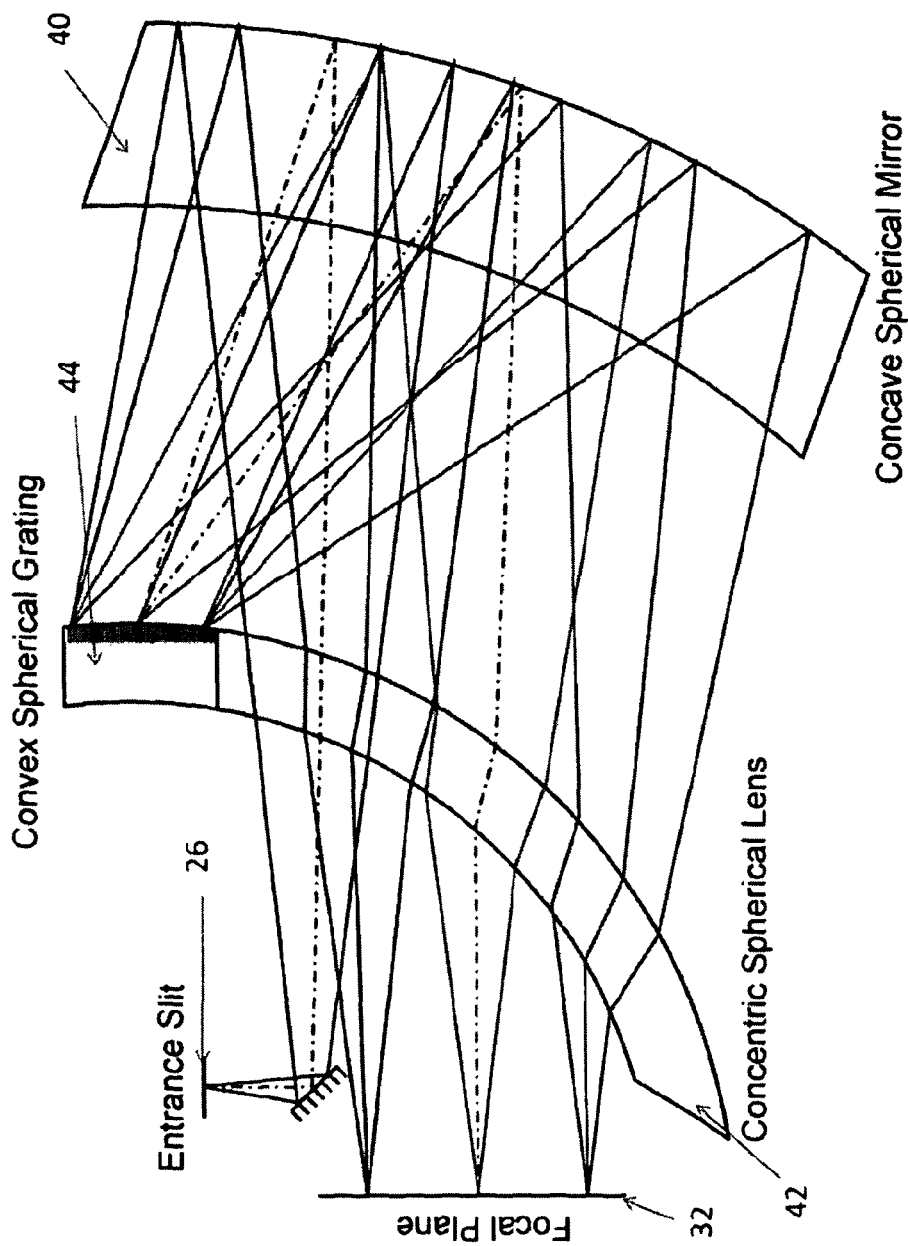
FIG. 3 is a diagrammatic representation of the optical assembly of the spectrometer assembly of FIG. 2.

Turning to FIG. 3, one arrangement of the optical assembly 24 of the system 2 is shown in general diagrammatic form. The optical assembly 24 comprises the mirror assembly 28 having a concave spherical mirror 40. The lens assembly 30 comprises a spherical lens 42, mounted alongside the grating assembly 26 having a concave spherical grating 44. The mirror 40, lens 42 and grating 44 are arranged concentrically about a common axis of curvature. As shown in FIG. 3, light passing through the slit of the entrance optical assembly 22 passes through the lens and on to the mirror 40. Light reflected from the mirror is incident on the grating 44, from where the light rays are returned to the mirror, being reflected again to pass through the lens and focussed onto the detector 32.

Figure 4:
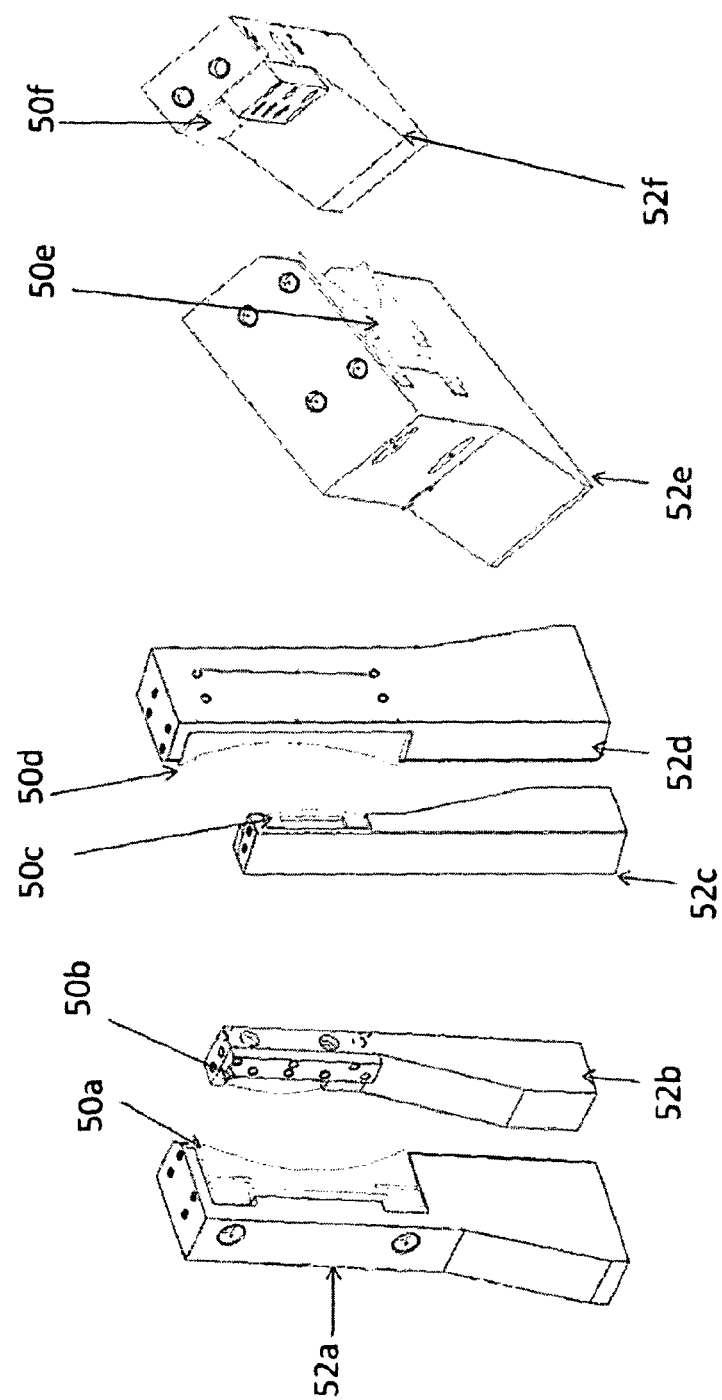
FIG. 4 is a perspective view of the entrance optical assembly of the spectrometer of FIG. 2.

The entrance optical assembly 22 is shown in more detail in FIG. 4. The entrance optical assembly 22 comprises an entrance slit (not shown for clarity) in combination with a plurality of entrance telescope mirrors 50a to 50f each mounted on a respective support 52a to 52f. The entrance slit may be formed in conventional manner or as a sealed window and is mounted so as to be adjustable, preferably with one or more screws, so as to allow the optical components of the system to be aligned. Adjustment of the entrance slit is provided for three planes to an accuracy of +/−0.5 mm, together with rotational accuracy of +/−1°. The entrance slit has a length of approximately 30 mm and a width of 70 to 120 μm, with an accuracy of +/−2 μm. The full width half maximum (FWHM) of the spectral profile of the spectrometer assembly is determined by the width of the entrance slit. The width of the entrance slit may be varied in order to optimise the spectral resolution of the spectrometer with respect to the target components in the atmosphere. If the housing of the spectrometer assembly is evacuated or purged, the entrance slit may be formed as a window, for example as a graticule on a UV/VIS transmitting window.

The entrance telescope mirrors 50a to 50f are turned from aluminium using diamond tools and are mounted in their respective mounts so as to be adjustable in the same manner as the entrance slit. The entrance telescope mirrors 50a to 50f are arranged to focus the incident light entering the housing along the length of the entrance slit.

The entrance optical system provides the spectrometer assembly with a field of view of 95°, having a width of 0.5°. The entrance optical system is arranged with the upper edge of the field of view to be at the zenith, so as to allow the field of view to extend from the zenith to 5° below the horizon.

Figure 5:
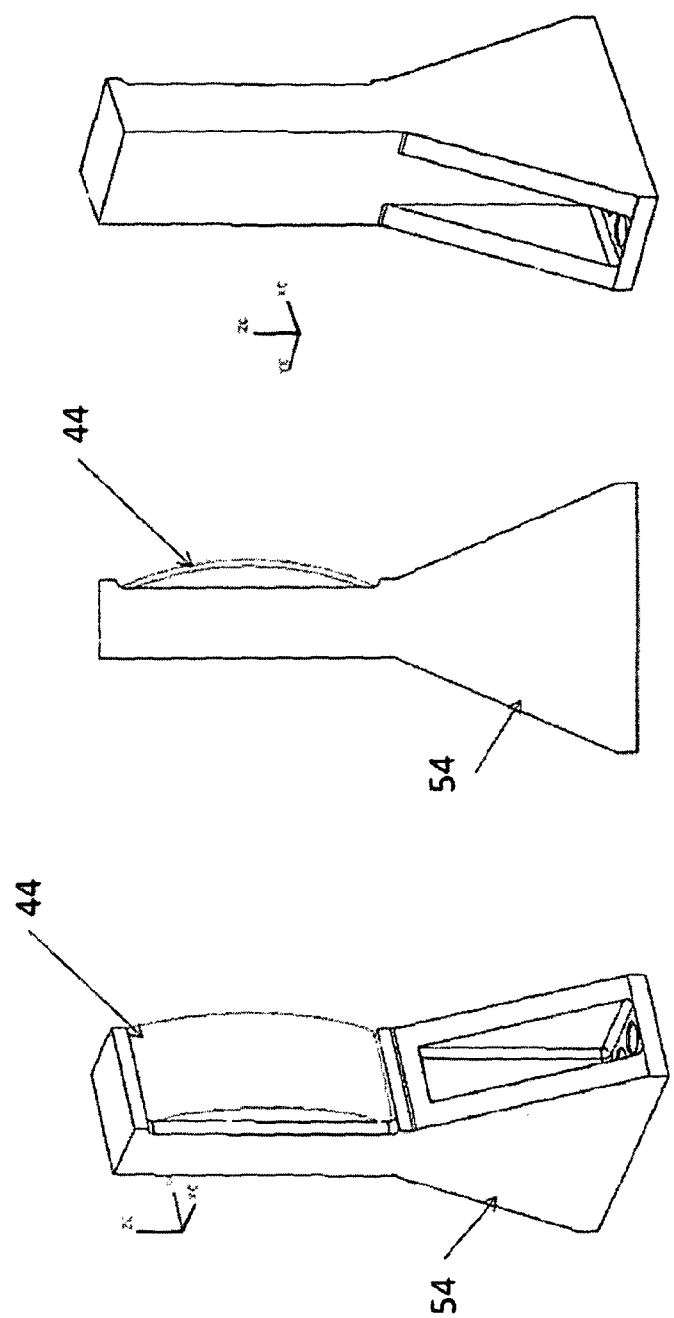
FIG. 5 is a perspective view of the grating assembly of the spectrometer of FIG. 2.

The grating assembly 26 is shown in more detail in the perspective views shown in FIG. 5 and comprises the concave spherical grating 44 supported by a mount 54. The grating 44 is formed from fused silica and has planar surfaces on the side opposite the spherical grating. The grating 44 is fixed to the mount 54 without the facility for adjustment thereof.

Figure 6:
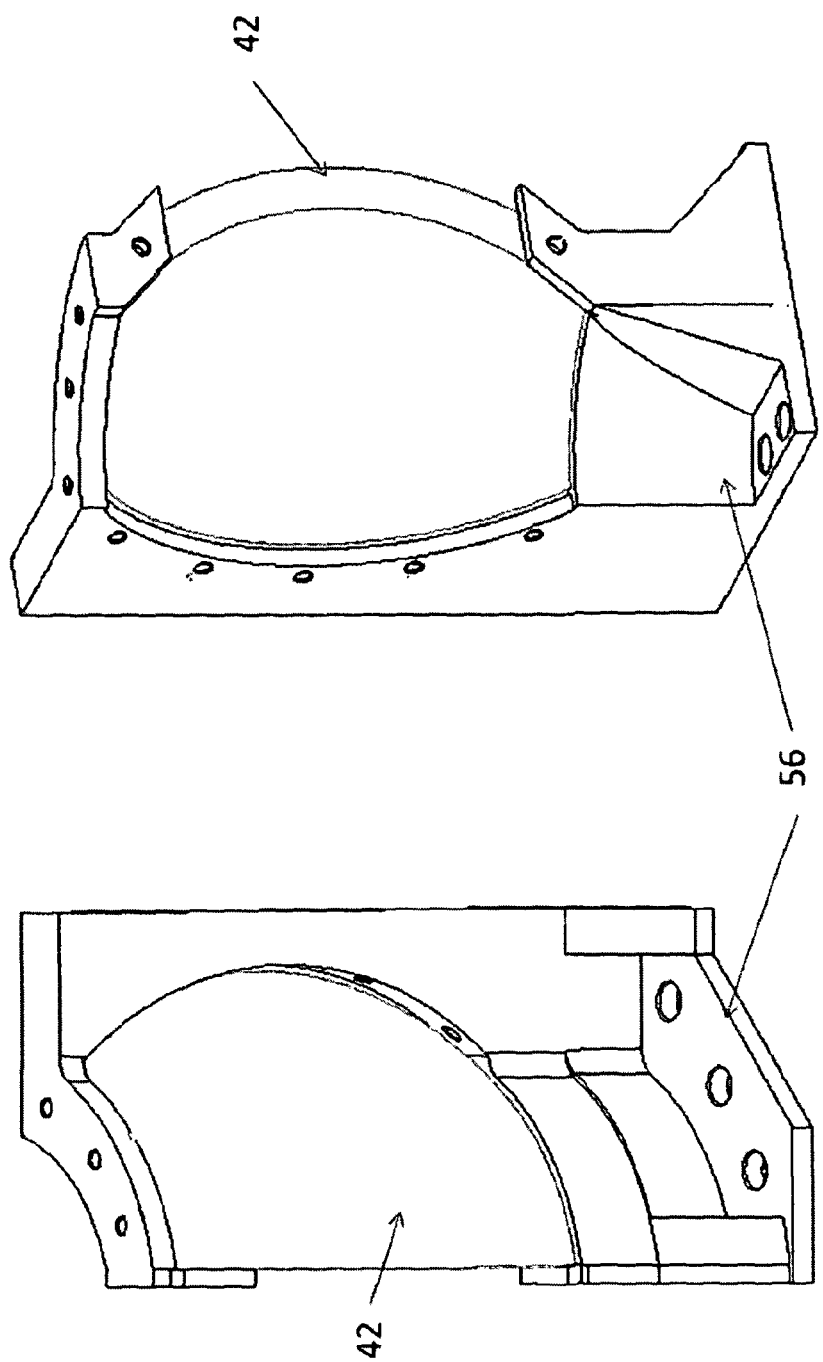
FIG. 6 is a perspective view of the lens assembly of the spectrometer of FIG. 2.

The lens assembly 30 is located adjacent the grating assembly 26, as shown schematically in FIG. 3. The lens assembly 30 is shown in more detail in the perspective views in FIG. 6 and comprises the spherical lens 42 supported in a mount 56. The lens is formed from fused silica and has both front and rear surfaces highly polished. The lens is mounted so as to be rotationally adjustable in all three axes by about 1°. In addition, the lens mount allows for translational adjustment of the position of the lens along three axes. Once aligned within the spectrometer assembly, the lens may be cemented in place in the mount 56.

Figure 7:
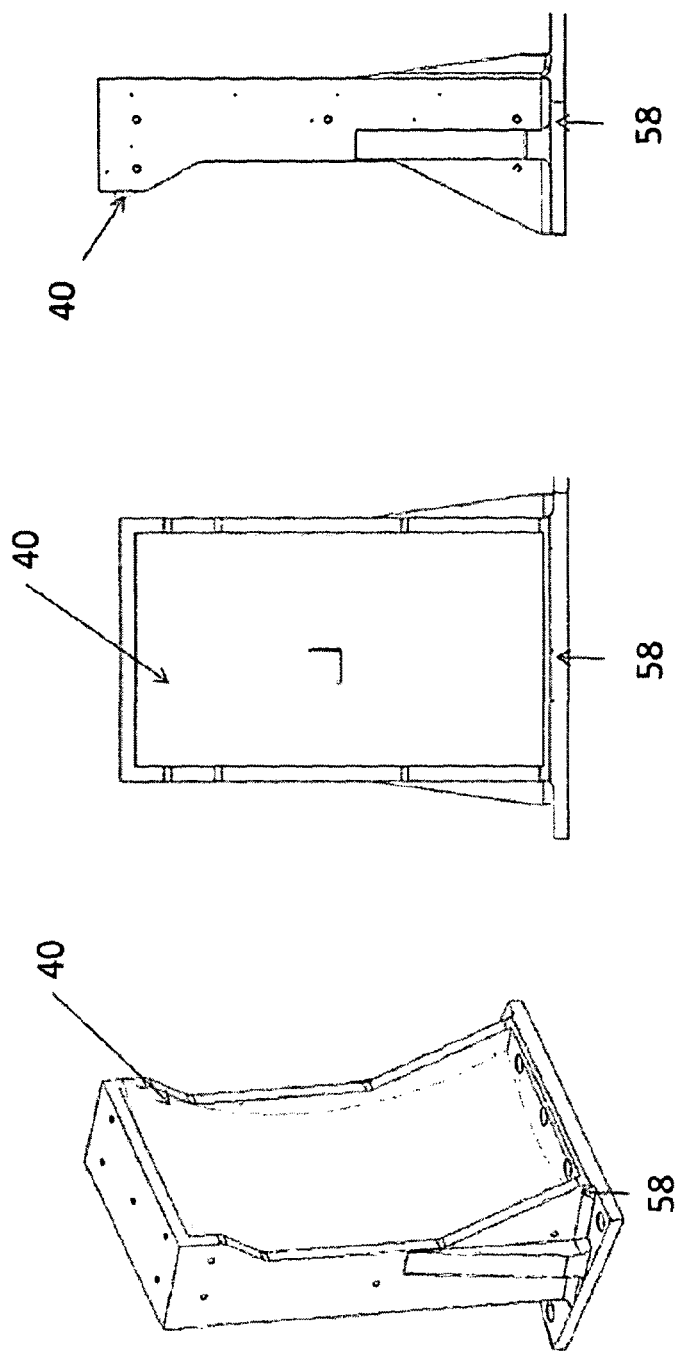
FIG. 7 is a perspective view of the mirror assembly of the spectrometer of FIG. 2.

The mirror assembly 28 is shown in more detail in the perspective views of FIG. 7 and comprises the concave spherical mirror 40 supported on a suitable mount 58. The mirror is formed from fused silica with an aluminium mirrored face. The mirror 40 is mounted to have translational adjustment in three planes. However, the mirror does not require rotational adjustment. As with the lens, once adjusted and in position, the mirror can be cemented in place.

The detector 32 is a CCD detector having a focal plane of 31×31 mm, covering the wavelength range of from 420 to 590 nm, selected to respond to the presence of nitrogen oxides in the region of atmosphere being scanned by the system. The detector is positioned to be at the focal plane of the optical assembly and is located in the same plane as the entrance slit. The detector 32 is supported in a mount (not shown in FIGS. 2a and 2b for clarity) so as to be adjustable in three planes to an accuracy of +/−0.5 mm, together with rotational accuracy of +/−1°. The detector is provided with a cooler, to remove heat accumulated in the detector during operation.

The system further comprises a processor 60, disposed within the base 4. The processor 60 receives signals from the detector 32 and processes the signals to generate data relating to the identity of components in the atmosphere in the region being scanned, their position and/or their concentration, together with changes in the same over time. Data are output by the processor in any suitable form, either locally to a user/operator or to a remote location. In a preferred arrangement, the processor 60 operates to generate data in the form of an image of the region being scanned.

As shown in FIG. 1, the spectrometer assembly 10 is housed within a protective covering allowing the ingress of incident diffuse solar radiation, in this case a dome 62. The fidelity of the protective covering determines the spatial resolution achievable by the spectrometer assembly.

Figure 8:
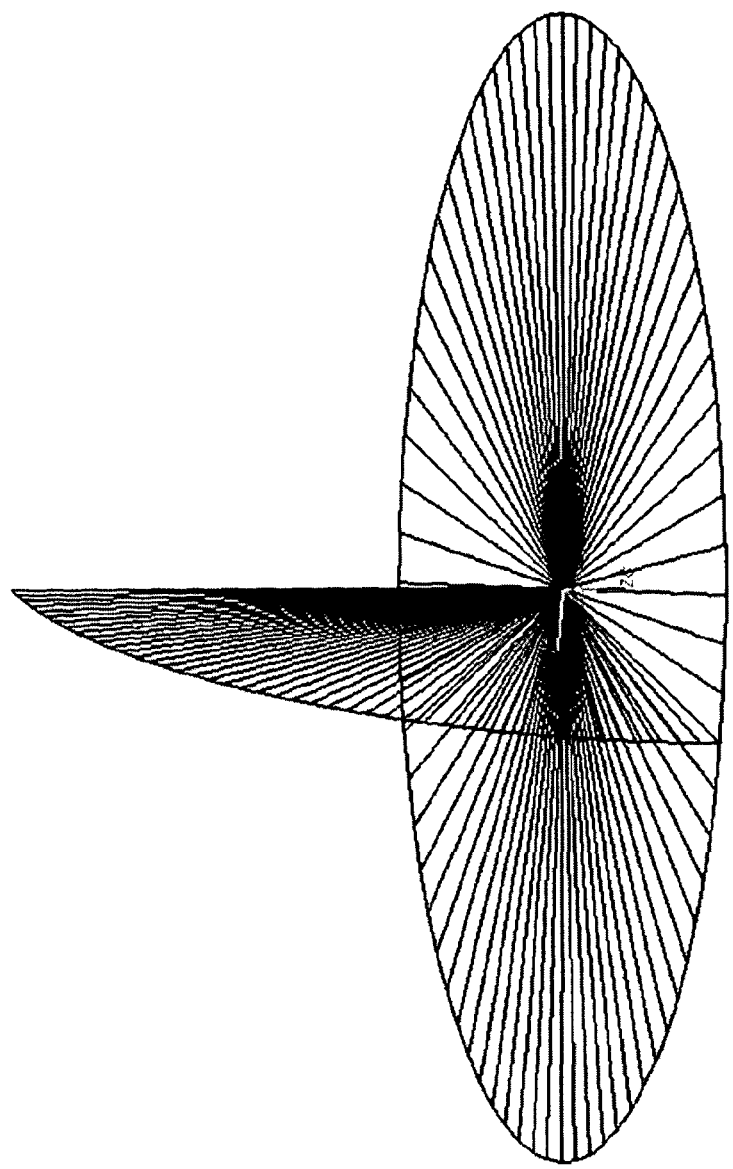
FIG. 8 is a representation of the system of FIG. 1 scanning a region of the atmosphere.

In operation, the spectrometer assembly 10 is rotated by the motor assembly 8. Sunlight enters the spectrometer housing and is processed in the optical assemblies as described above to be focussed upon the detector 32. With the spectrometer assembly 10 is one position, the system provides data relating to a portion of the region of the atmosphere as shown in FIG. 8. FIG. 8 shows a typical scanning pattern of the system of the present invention superimposed on a photograph of a town. As the spectrometer assembly 10 rotates with the turntable, successive portions are scanned providing data relating to a complete hemisphere extending around the location of the system. With a field of view of 95° and a width of 0.5°, arranged as described above with respect to the zenith, the system provides a rotational resolution of 1°, with one full rotation of the spectrometer assembly taking 6 minutes. The field of view is divided into 500 resolved segments, with each resolved element corresponding to 0.19° of the field of view.

Figure 9:
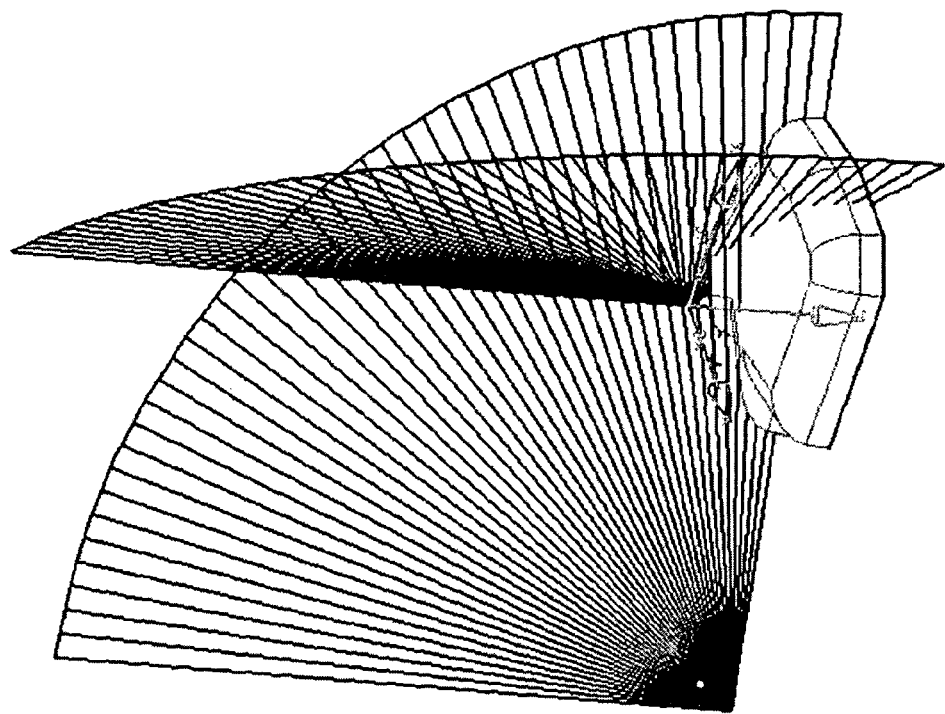
FIG. 9 is a representation of two systems according to FIG. 1 being used to provide tomographic monitoring of a region of the atmosphere.

Finally, two systems are shown being operated in configuration in FIG. 9, to provide scans of overlapping regions of the atmosphere, allowing for a tomographical analysis of the region to be obtained. FIG. 9 shows the scanning patterns of two systems of the present invention superimposed on a photograph of a town.

The invention claimed is:

1. A system for detection of components in a region of an atmosphere, the system comprising:
    a spectrometer assembly having a detector optically coupled to an optical assembly, the optical assembly receiving incident sunlight from the region of the atmosphere, the optical assembly having a field of view extending from a zenith to below a horizon;
    a turntable coupled to the spectrometer assembly for rotating the spectrometer assembly about a vertical axis; and
    a processor for receiving data from the spectrometer assembly and compiling data relating to an identity and concentration of components in the region of the atmosphere.

2. The system according to claim 1, wherein the spectrometer assembly is arranged to detect pollutants in the atmosphere.

3. The system according to claim 2, wherein the pollutants are products of combustion of a hydrocarbon fuel.

4. The system according to claim 3, wherein the pollutants are one or more oxides of nitrogen or sulphur.

5. The system according to claim 1, wherein the spectrometer assembly is a differential optical absorption spectroscopy (DOAS) system.

6. The system according to claim 1, wherein the detector is a CCD or CMOS detector.

7. The system according to claim 1, wherein the detector has a target focal plane arranged to receive light of wavelengths in a range of from 420 to 590 nm.

8. The system according to claim 1, wherein the optical assembly is a concentric optical assembly.

9. The system according to claim 8, wherein the optical assembly comprises a spherical mirror, a spherical lens and a spherical grating all arranged concentrically.

10. The system according to claim 1, wherein the optical assembly comprises an entrance optical assembly that is aspheric.

11. The system according to claim 1, wherein the field of view of the spectrometer assembly extends from the zenith to at least 5' below the horizon.

12. The system according to claim 1, wherein the field of view is of at least 95°.

13. The system according to claim 1, wherein the field of view has a width of 0.5°.

14. The system according to claim 1, wherein the field of view of the spectrometer is divided into at least 500 resolved elements.

15. The system according to claim 1, wherein the spectrometer assembly is mounted on a turntable and rotatable therewith.

16. The system according to claim 1, wherein the spectrometer assembly is able to be rotated through a full 360° rotation or a part thereof.

17. The system according to claim 1, wherein means are provided to avoid incidence of direct sunlight on the spectrometer assembly.

18. The system according to claim 1, wherein the spectrometer assembly is arranged to detect concentration of one or more products of combustion of hydrocarbon fuels, the processor being configured to generate therefrom estimates of a level of emissions of target components in the region being scanned.

19. The system according to claim 18, comprising two, three or more than three systems, all the systems being arranged such that their scanned regions overlap.

20. An atmospheric monitoring system comprising a plurality of systems as claimed in claim 1, the systems being arranged such that their scanned regions overlap.

21. A method of monitoring pollutants in a region of an atmosphere, the method comprising:
providing a spectrometer assembly having a detector optically coupled to an optical assembly having a field of view extending from a zenith to below a horizon;
exposing the spectrometer assembly to incident sunlight while rotating the spectrometer assembly about a substantially vertical axis; and
processing signals received from the spectrometer assembly to analyse components in the atmosphere.

22. The method according to claim 21, wherein the spectrometer has a field of view of 95°.

23. The method according to claim 21, wherein the field of view of the spectrometer is divided into at least 500 resolved elements.

24. The method according to claim 21, wherein the pollutants are products of combustion of a hydrocarbon fuel.

25. The method according to claim 24, wherein the pollutants are one or more oxides of nitrogen or sulphur.

26. The method according to claim 24, wherein the spectrometer assembly determines a concentration of one or more products of combustion in the region being scanned, and a processor generates therefrom an estimate of a level of emissions within the region.

27. The method according to claim 21, wherein the spectrometer is rotated through 360°.

28. The method according to claim 21, wherein incidence of direct sunlight onto the spectrometer is avoided.

29. The method according to claim 21, wherein a plurality of spectrometer assemblies are employed, the region scanned by the spectrometer assemblies overlapping.

* * * * *